United States Patent
Cichocki, Jr. et al.

(10) Patent No.: US 11,612,392 B2
(45) Date of Patent: Mar. 28, 2023

(54) SYSTEMS, DEVICES AND METHODS OF MAKING HIGHLY ELASTIC SUTURE NEEDLES FOR MINIMALLY INVASIVE SURGERY

(71) Applicant: Ethicon, Inc., Somerville, NJ (US)

(72) Inventors: Frank Richard Cichocki, Jr., Easton, PA (US); Christophe Vailhe, Hillsborough, NJ (US); Alexander M. Cannara, Roseland, NJ (US)

(73) Assignee: Ethicon, Inc., Raritan, NJ (US)

( * ) Notice: Subject to any disclaimer, the term of this patent is extended or adjusted under 35 U.S.C. 154(b) by 109 days.

(21) Appl. No.: 16/781,055

(22) Filed: Feb. 4, 2020

(65) Prior Publication Data

US 2020/0268380 A1   Aug. 27, 2020

Related U.S. Application Data

(60) Provisional application No. 62/809,016, filed on Feb. 22, 2019.

(51) Int. Cl.
 *A61B 17/06* (2006.01)
 *A61B 17/04* (2006.01)
 *A61B 17/00* (2006.01)

(52) U.S. Cl.
 CPC .... *A61B 17/06066* (2013.01); *A61B 17/0469* (2013.01); *A61B 17/06004* (2013.01);
 (Continued)

(58) Field of Classification Search
 CPC . A61B 17/06; A61B 17/0469; A61B 17/0482; A61B 17/06066; A61B 17/06004; A61B 2017/0472; A61B 2017/06047
 See application file for complete search history.

(56) References Cited

U.S. PATENT DOCUMENTS 3,160,157 A   12/1964 Chisman
3,265,070 A   8/1966 Kurtz
(Continued)

FOREIGN PATENT DOCUMENTS

CN   201755238   3/2011
CN   201782788   4/2011
(Continued)

OTHER PUBLICATIONS

Cichocki et al., "Tungsten-Rhenium Suture Needles With Improved Properties for Coronary Artery Bypass Graft Surgery," Journal of Biomedical Materials Research B: Applied Biomaterials, Aug. 2010, pp. 493-500, vol. 94B, Issue 2.
(Continued)

*Primary Examiner* — Tuan V Nguyen

(57) ABSTRACT

An elastic suture needle for passing through a smaller cannula used in minimally invasive surgery includes an elongated body having a proximal end, a distal end, a length extending from the proximal end to the distal end, a top surface extending along the length of the elongated body, and a bottom surface extending along the length of the elongated body. The elongated body has dimensions that are calculated using the equation $T/L_N < (4^*\sigma)/(\pi E)$, where T is the thickness of the elongated body, $L_N$ is the length of the neutral axis of the elongated body, $\sigma$ is the yield strength of the elongated body, and E is the Young's modulus of the elongated body. The elongated body is made of stainless steels such as martensitic stainless steels, austenitic stainless steels, martensitic-aged (mar-aged) stainless steels, and stainless steels sold under the registered trademark ETHAL-LOY® Needle Alloy.

18 Claims, 10 Drawing Sheets

(52) U.S. Cl.
CPC .............. *A61B 2017/00526* (2013.01); *A61B 2017/0608* (2013.01); *A61B 2017/06095* (2013.01)

(56) References Cited

U.S. PATENT DOCUMENTS

| | | | |
|---|---|---|---|
| 4,327,655 | A | 5/1982 | Addy et al. |
| 5,041,127 | A | 8/1991 | Troutman |
| 5,059,207 | A * | 10/1991 | Shah ................ A61B 17/06066 223/102 |
| 5,219,358 | A * | 6/1993 | Bendel ............... A61B 17/0469 606/222 |
| 5,269,806 | A | 12/1993 | Sardelis et al. |
| 5,897,572 | A | 4/1999 | Schulsinger et al. |
| 5,928,268 | A * | 7/1999 | Butwell .................. B21G 1/08 606/222 |
| 5,935,138 | A | 8/1999 | McJames, II et al. |
| 6,322,581 | B1 | 11/2001 | Fakuda et al. |
| 7,727,257 | B2 | 6/2010 | Loubens et al. |
| 7,937,981 | B2 | 5/2011 | Reynolds et al. |
| 8,066,737 | B2 | 11/2011 | Meade et al. |
| 8,883,245 | B2 | 11/2014 | Cichocki et al. |
| 2003/0144674 | A1 * | 7/2003 | Loubens ............... A61B 17/062 606/148 |
| 2004/0002724 | A1 | 1/2004 | Falahee |
| 2008/0147118 | A1 * | 6/2008 | Cichocki .................. B21G 1/08 606/223 |
| 2010/0198256 | A1 | 8/2010 | Loubens et al. |
| 2012/0010655 | A1 | 1/2012 | Lin |

FOREIGN PATENT DOCUMENTS

| | | |
|---|---|---|
| CN | 204839615 | 12/2015 |
| CN | 204863323 | 12/2015 |
| CN | 206777363 | 12/2017 |
| EP | 0437329 | 7/1991 |
| EP | 0529675 | 3/1993 |

OTHER PUBLICATIONS

"Nitinol . . . . The Material of Choice for Safer, More Effective Medical Procedures", Announcement, Flexmedics Corporation, Jan. 1, 1989, 3 pages, XP002918035.

Arvind Midha et al., "Martensitic Age-Hardenable Stainless Steel: Veratility for Wide Array of Applications", Advanced Materials & Processes, Sep. 1, 2011, pp. 30-33, vol. 168, No. 9, XP055682789.

International Search Report issued in corresponding International Application No. PCT/IB2020/050877, Apr. 17, 2020, 4 pages.

* cited by examiner

SYSTEMS, DEVICES AND METHODS OF MAKING HIGHLY ELASTIC SUTURE NEEDLES FOR MINIMALLY INVASIVE SURGERY

CROSS-REFERENCE TO RELATED APPLICATIONS

The present patent application claims benefit of commonly assigned U.S. Provisional Application Ser. No. 62/809,016, filed on Feb. 22, 2019, the disclosure of which is hereby incorporated by reference herein.

BACKGROUND OF THE INVENTION

Field of the Invention

The present patent application is generally related to surgical procedures and surgical tools, and is more specifically related to systems, devices and methods of making and using elastic suture needles that are passed through lumens such as those associated with trocars and cannulas (hereinafter referred to as cannulas).

Description of the Related Art

Surgeons use lumens such as cannulas to position surgical tools, such as suture needles, at surgical sites. The size of a suture needle that can be passed through a cannula is limited by the size of the opening in the cannula. In many instances, surgeons desire to use larger suture needles (i.e., suture needles that are larger than the cannula opening) for closing surgical wounds and repairing anatomical features, however, passing larger needles through smaller cannulas is difficult.

5 mm cannulas are often used during minimally invasive surgeries (MIS), however, surgeons cannot pass the larger suture needles through the 5 mm cannulas so they are forced to use only smaller suture needles. The smaller suture needles are less than optimal because, inter alia, they often require a surgeon to make many more passes of the needle and suture through tissue, which lengthens the surgical procedure and can frustrate the surgeon. Using smaller needles may also produce a bite distance that puts the wound or anatomical feature at risk of dehiscence.

Another drawback of using smaller suture needles is that larger sized sutures cannot be easily attached to the smaller suture needles. This often forces surgeons to use smaller sized sutures than required for a suturing operation. Thus, when fine or smaller sized sutures are passed through tissue with a smaller bite size, a cheese wire effect may result, whereby the suture cuts through the tissue it is intended to hold.

In an effort to resolve one or more of the above-noted problems, advances have been made to provide suture needles made of superelastic alloys having shape memory properties, which enable a curved suture needle to be straightened for being passed through a cannula. When the superelastic suture needle is removed from the other end of the cannula for use at a surgical site, the shape memory properties of the needle return it back to the original curved shape.

An alloy commonly referred to as Nitinol is often used to make superelastic suture needles. Suture needles made of Nitinol, however, can be very difficult to process, which results in high production costs that are often charged to customers, and which could substantially limit the adoption of Nitinol suture needles for minimally invasive surgeries.

In addition, there are many challenges associated with securing sutures to the suture attachment barrels of Nitinol suture needles. These challenges include the tendency of the suture attachment barrels of Nitinol needles to spring back after a swaging step, which results in the formation of a weak attachment between the suture and the Nitinol suture needle.

Thus, there remains a need for improved suture needles, not made of Nitinol, that exhibit elasticity so that larger suture needles may be passed through relatively smaller cannulas (e.g., 5 mm cannulas) for use in surgical procedures. There also remains a need for elastic suture needles that may be passed through smaller cannulas and not be plastically deformed. In addition, there is a need for systems, devices and methods of making larger suture needles made of stainless steels that can be elastically deformed for passing through the relatively smaller cannulas for use in minimally invasive surgery.

SUMMARY OF THE INVENTION

In one embodiment, a suture needle having a large size and conventional curvature (e.g., ½ circle) may be passed through a lumen such as a cannula. The suture needle is elastically straightened as it is passed through the cannula and the springs back to its original curvature upon being removed from an end of the cannula for use in surgery.

In one embodiment, a suture needle may be produced from alloys that are not superelastic. In one embodiment, the suture needle may be made of alloys such as ETHALLOY® Needle Alloy (martensitic-aged stainless steel) or 4310 (austentic work-hardened stainless steel) to accomplish the same net effect of elastic recovery after cannula passage that a superelastic Nitinol needle provides.

In one embodiment, the term "elongated body" means a section of a suture needle having a top surface (e.g., a flat top surface) and a bottom surface (e.g., a flat bottom surface), whereby the top and bottom surfaces extend between proximal and distal ends of the elongated body. In one embodiment, a suture needle may include a suture attachment barrel that is integral to the proximal end of the elongated body and a tip (e.g., a pointed or sharpened tip) that is integral to the distal end of the elongated body. In one embodiment, the suture attachment barrel and the tip are not considered to be part of the elongated body.

In one embodiment, an elastic suture needle preferably includes an elongated body having a proximal end, a distal end, a length $L_N$ along a neutral axis extending from the proximal end to the distal end of the elongated body, a top surface extending along the length of the elongated body, and a bottom surface extending along the length of the elongated body. In one embodiment, the neutral axis is defined as the axis at which strain (and consequently stress) is zero in the elongated direction of the body when the beam is subjected to bending.

In one embodiment, the elongated body of the elastic suture needle preferably has dimensions that are calculated using the equation $T/L_N < (4^*\sigma)/(\pi E)$, where T is the thickness of the elongated body, $L_N$ is the neutral length of the elongated body, $\sigma$ is the yield strength of the elongated body, and E is the Young's modulus of the elongated body.

In one embodiment, the top and bottom surfaces of the elongated body are used to define the thickness T of the elongated body. In one embodiment, the top and bottom surfaces of the elongated body may have shapes other than flat surfaces including but not limited to top and bottom convex surfaces, top and bottom concave surfaces, top and bottom ribbed surfaces, and top and bottom surfaces that are a combination of convex and concave shapes (e.g., a concave top surface and a convex bottom surface) and ribbed surfaces.

In one embodiment, the elongated body of the suture needle is preferably made of stainless steel, such as martensitic stainless steels, austenitic stainless steels, martensitic-aged (mar-aged) stainless steels, and/or stainless steels sold under the registered trademark ETHALLOY® Needle Alloy.

In one embodiment, the elongated body of the suture needle is preferably made of a martensitic-aged stainless steel having a yield strength of about 1500-2200 MPa and a Young's modulus of about 200-205 GPa.

In one embodiment, the thickness T of the elongated body is defined as a distance between the outermost top surface of the elongated body and the outermost bottom surface of the elongated body.

In one embodiment, the top surface of the elongated body preferably includes a flat top surface that extends along the length of the elongated body. In one embodiment, the bottom surface of the elongated body preferably includes a flat bottom surface that extends along the length of the elongated body. In one embodiment, the thickness T of the elongated body is preferably a distance between the flat top surface and the flat bottom surface of the elongated body.

In one embodiment, the elastic suture needle desirably includes a tip that is located at the distal end of the elongated body. In one embodiment, the tip is integral with the distal end of the elongated body. The tip may define the leading or distal-most end of the elastic suture needle. The tip may be sharpened or may be a point.

In one embodiment, the elastic suture needle desirably includes a suture attachment barrel located at the proximal end of the elongated body. The suture attachment barrel may be integral with the proximal end of the elongated body. The suture attachment barrel may have an opening adapted to receive an end of a suture so that a suture may be attached to a proximal end of the suture needle.

In one embodiment, the elongated body of the suture needle is curved along its length with the top surface of the elongated body defining the concave aspect of the curve and the bottom surface of the elongated body defining the convex aspect of the curve.

In one embodiment, an elastic suture needle preferably includes an elongated stainless steel body having a proximal end, a distal end, a neutral axis extending from the proximal end to the distal end of the elongated body, a flat top surface extending along the length of the elongated stainless steel body, and a flat bottom surface extending along the length of the elongated stainless steel body.

In one embodiment, the elongated body desirably has dimensions that are calculated using the equation $T/L_N < (4*\sigma)/(\pi E)$, where T is the thickness defined as a distance from the flat top surface to the flat bottom surface of the elongated stainless steel body, $L_N$ is the length of the neutral axis of the elongated stainless steel body between the proximal and distal ends thereof, $\sigma$ is the yield strength of the elongated stainless steel body, and E is the Young's modulus of the elongated stainless steel body.

In one embodiment, the elongated stainless steel body is preferably curved with the flat top surface of the elongated stainless steel body defining a concave curved surface and the flat bottom surface of the elongated stainless steel body defining a convexly curved surface.

In one embodiment, the elongated stainless steel body is desirably made of a martensitic-aged stainless steel having a yield strength of about 1500-2200 MPa and a Young's modulus of about 200-205 GPa.

In one embodiment, a method of making an elastic suture needle desirably includes obtaining an elongated body having a proximal end, a distal end, a top surface extending between the proximal and distal ends, and a bottom surface extending between the proximal and distal ends, whereby the elongated body is made of a material having a predetermined yield strength and a predetermined Young's modulus.

In one embodiment, a method of making the elastic suture needle preferably includes using the equation $T/L_N < (4*\sigma/E)$ for determining a thickness and a length of the elongated body, where T is the thickness of the elongated body that is defined as a distance from the top surface to the bottom surface of the elongated body, $L_N$ is the neutral length of the elongated body that extends from the proximal end to the distal end of the elongated body, $\sigma$ is the yield strength of the elongated body, and E is the Young's modulus of the elongated body.

In one embodiment, the elongated body is made of stainless steel such as martensitic stainless steels, austenitic stainless steels, martensitic-aged (mar-aged) stainless steels, and stainless steels sold under the registered trademark ETHALLOY Needle Alloy.

In one embodiment, the top surface of the elongated body desirably includes a flat top surface that extends along the length of the elongated body, and the bottom surface of the elongated body desirably includes a flat bottom surface that extends along the length of the elongated body. In one embodiment, the thickness T of the elongated body is a distance between the flat top surface of the elongated body and the flat bottom surface of the elongated body.

In one embodiment, the elastic suture needle preferably has a curved shape defining a first height $H_1$.

In one embodiment, the method includes obtaining a cannula having a proximal end, a distal end, and a conduit that extends from the proximal end to the distal end of the cannula, whereby the conduit of the cannula has an inner diameter defining a second height $H_2$ that is less than the first height $H_1$ of the elastic suture needle.

In one embodiment, a method includes with the elastic suture needle at the first height $H_1$, positioning the elastic suture needle adjacent the proximal end of the cannula.

In one embodiment, a method preferably includes passing the elastic suture needle through the conduit and from the proximal end to the distal end of the cannula, whereby during the passing step the elastic suture needle flattens out for transforming to a third height $H_3$ that is less than or equal to the second height $H_2$ of the conduit.

In one embodiment, after the passing step, the elastic suture needle is preferably removed from the distal end of the cannula whereupon the elastic suture needle transforms back to a curved shape having a fourth first height $H_4$ that is greater than the second height $H_2$ of the conduit. In one embodiment, the fourth height $H_4$ is about 90% of the original, first height $H_1$. In one embodiment, the fourth height $H_4$ is about 95% of the original, first height $H_1$. In one embodiment, the fourth height $H_4$ is equal to the original, first height $H_1$.

In one embodiment, the suture needle may be elastically deformed to lower the height and/or the profile of the suture needle to pass the suture needle through a cannula, such as a cannula having a diameter of 5 mm or smaller.

In one embodiment, a needle driver may be used to secure a distal end of the suture needle with the barrel of the suture needle trailing behind the tip of the suture needle. In one embodiment, the tip is preferably surrounded by clamping jaws at the distal end of the needle driver for protecting the tip as the suture needle is passed through a cannula. The clamping jaws preferably surround and protect the tip for preventing the tip from contacting the inside of the cannula as it is passed through the cannula, thereby avoiding damage to the tip during its passage through the cannula.

In one embodiment, when the suture needle is held by the needle driver, the tip of the needle does not extend or protrude outside the external surface of the needle holder.

These and other preferred embodiments of the present invention will be described in more detail below.

BRIEF DESCRIPTION OF THE DRAWINGS

FIG. 1B-1 is a magnified cross-sectional view of a mid-section of the elongated body of the elastic suture needle shown in FIGS. 1A and 1B.

DETAILED DESCRIPTION OF PREFERRED EMBODIMENTS

Figure 1A:
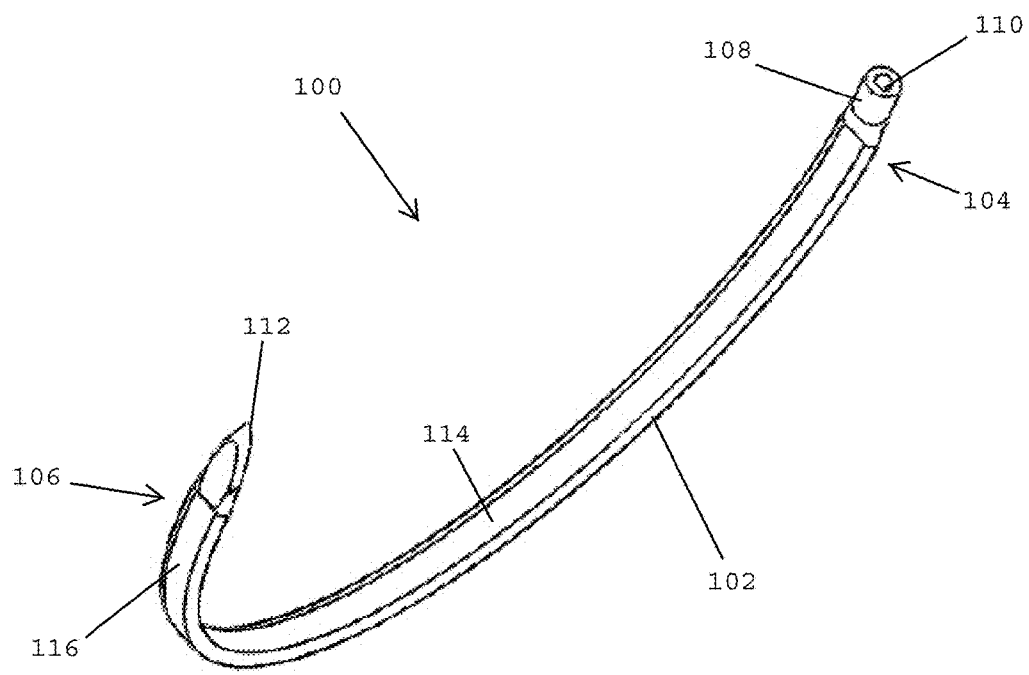
FIG. 1A is a perspective view of an elastic suture needle including an elongated body having a proximal end and a distal end, a suture attachment barrel integral to the proximal end of the elongated body, and a tip integral to the distal end of the elongated body, in accordance with one embodiment of the present patent application.
Figure 1B:
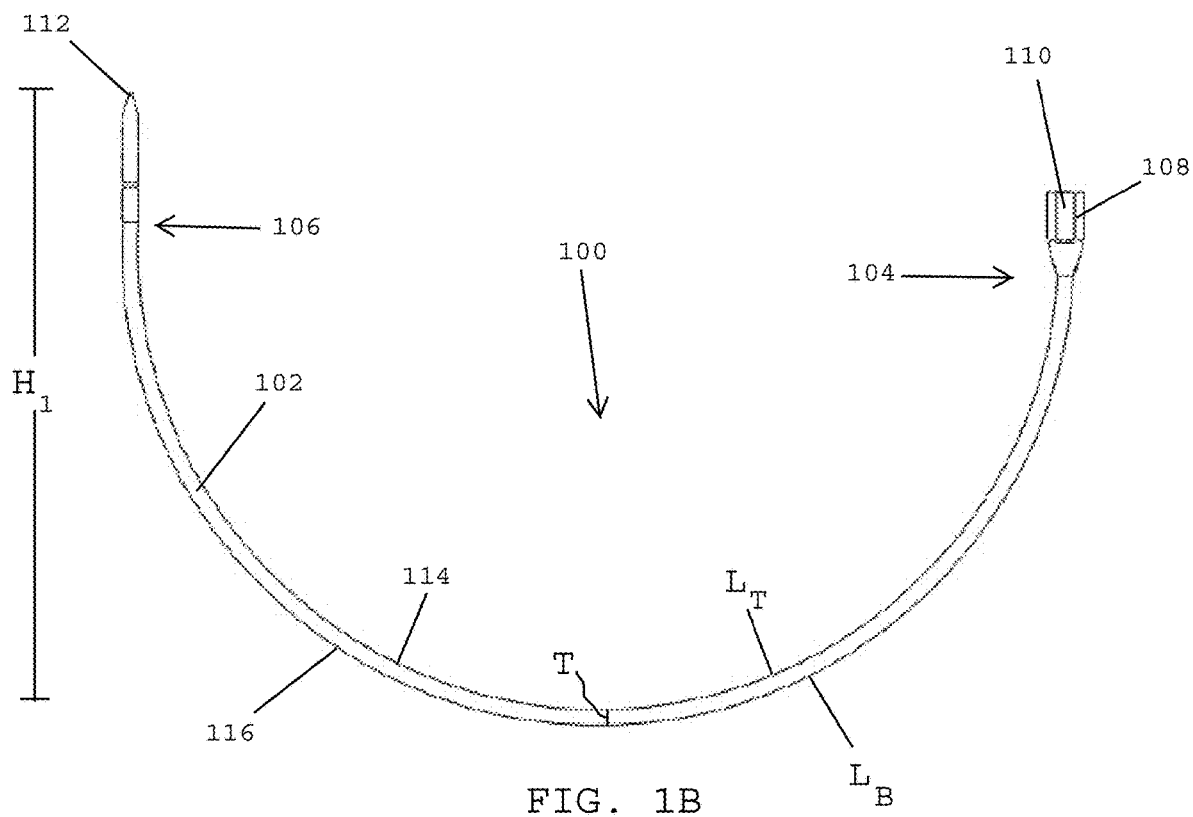
FIG. 1B is a side elevation view of the elastic suture needle having the elongated body shown in FIG. 1A.

Referring to FIGS. 1A and 1B, in one embodiment, an elastic suture needle 100 preferably includes an elongated body 102 having a proximal end 104 and a distal end 106. In one embodiment, the elongated body 102 of the suture needle 100 is curved. In one embodiment, the suture needle 100 defines a half circle or a semi-circle.

In one embodiment, the elastic suture needle 100 preferably includes a suture attachment barrel 108 that is adjacent the proximal end 104 of the elongated body 102, which preferably has a suture attachment opening 110 formed in a proximal face thereof. In one embodiment, a distal end of a surgical suture may be inserted into the suture attachment opening 110 of the suture attachment barrel 108 and the suture attachment barrel may be swaged for securing the surgical suture to the proximal end 104 of the elongated body 102 of the elastic suture needle 100.

In one embodiment, the elastic suture needle 100 preferably includes a tip 112, such as a sharpened or pointed tip, that is integral to the distal end 106 of the elongated body 102 and that preferably defines a leading or distal-most end of the suture needle 100. In one embodiment, the tip 112 is preferably sharpened for piercing tissue to facilitate passing the distal end 106 of the elongated body 102 of the suture needle 100 through tissue during a suturing operation.

In one embodiment, the elongated body 102 of the elastic suture needle 100 preferably includes a top surface 114 that extends along the inside of the curve of the curved elongated body 102 (i.e., the concave curved surface), and a bottom surface 116 that extends along the outside of the curve of the curved elongated body 102 (i.e., the convexly curved surface). The top and bottom surfaces 114, 116 of the elongated body 102 preferably define the thickness T of the elongated body 102 of the suture needle 100, whereby the axis for measuring the thickness T is perpendicular to the longitudinal axis of the elongated body 102 of the suture needle 100. In one embodiment, the top and bottom surfaces 114, 116 include flat surfaces that extend over the respective top and bottom sides of the elongated body of the suture needle. In other preferred embodiments, the top and bottom surfaces of the elongated body may include concave surfaces, convex surfaces, ribbed surfaces, and combinations of one concave surface and one convex surface, as will be described in more detail herein.

In one embodiment, the elongated body 102 of the elastic suture needle 100 is not made of a superelastic material, such as Nitinol, but is preferably made of stainless steel such as high strength stainless steel. In one embodiment, an external force (e.g., tension, compression) may be applied to the elastic suture needle to elastically deform the elongated body of the suture needle, and the elongated body of the suture needle will not be plastically deformed by the external force so that the elongated body will spring back to its original shape and/or configuration when the external force is removed.

Referring to FIG. 1B, in one embodiment, when the elastic suture needle 100 is in its original, half-circle configuration, the elongated body 102 of the elastic suture needle 100 defines a height $H_1$. As will be described in more detail herein, when external forces are exerted upon the outer surface of the elongated body 102 of the elastic suture needle 100 (e.g., when passing the suture needle through a cannula), the elongated body will preferably flex, bend, straighten, and/or flatten out for transforming into an elongated body having a lower height or profile than the original height $H_1$.

Figures 1, 1B:
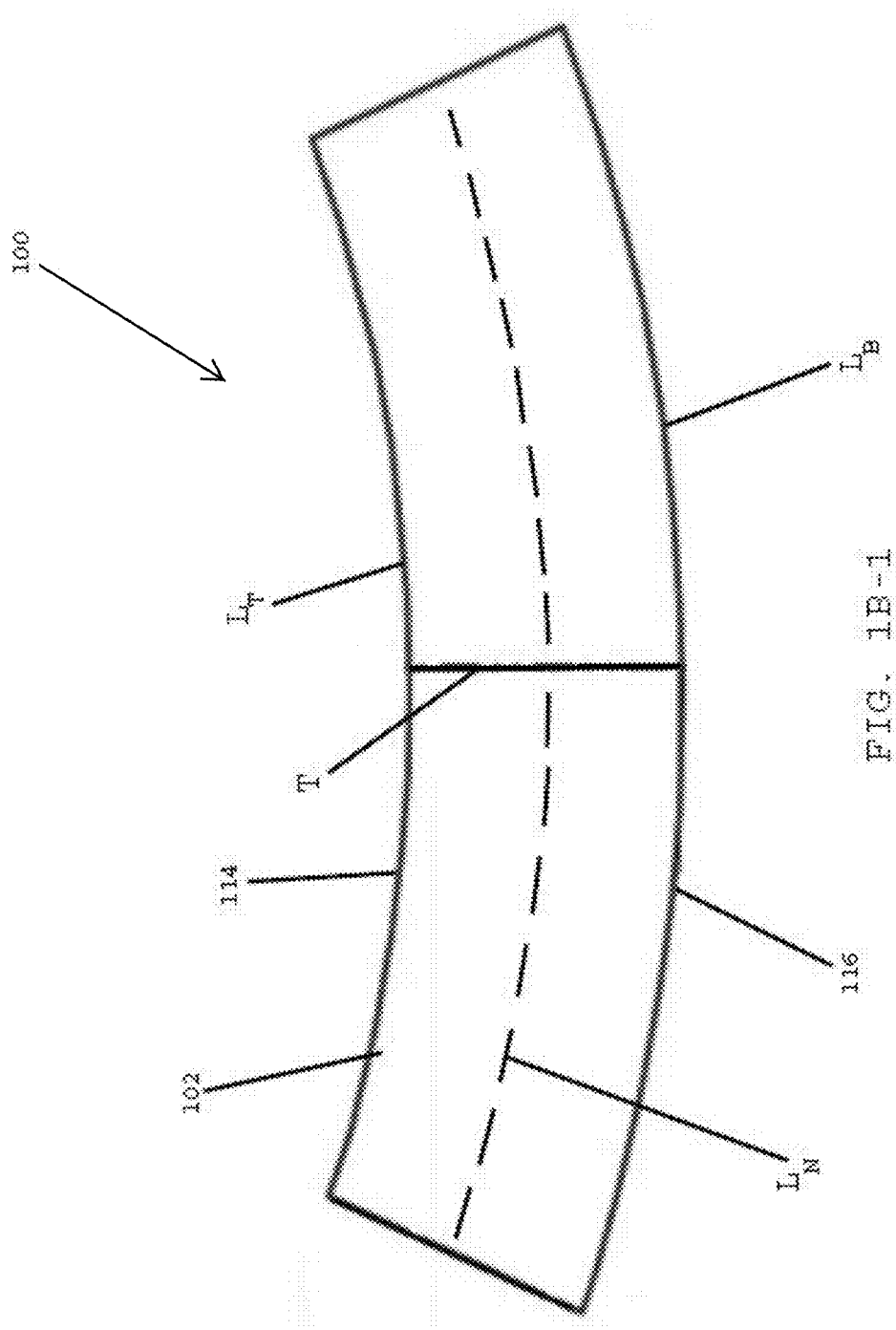

Referring to FIGS. 1B and 1B-1, in one embodiment, the elongated body 102 of the elastic suture needle 100 preferably has a length $L_N$ extending along the neutral axis of the elongated body 102 between the proximal end 104 and the distal end 106 (FIG. 1) hereinafter referred to as the neutral length of the suture needle 100. In one embodiment, the elongated body 102 of the elastic suture needle 100 preferably has a top length $L_T$ that extends along the top surface 114 of the elongated body 102 from the proximal end 104 to the distal end 106 of the elongated body, and a bottom length $L_B$ that extends along the bottom surface 116 of the elongated body 102 from the proximal end 104 to the distal end 106 of the elongated body 102.

In one embodiment, the neutral length $L_N$, the top length $L_T$ and the bottom length $L_B$ are the distances that extend from the proximal end 104 and the distal end 106 of the elongated body 102, and the extra lengths of the suture needle provided by the suture attachment barrel 108 and the tip 112 are not used to calculate the respective lengths $L_N$, $L_T$, and $L_B$ of the elongated body 102 of the suture needle 100.

In one embodiment, the elongated body of the elastic suture needle may have a bendable region provided thereon, which facilitates changing the shape and/or configuration of the suture needle to fit through a cannula (e.g., a 5 mm cannula), as disclosed in commonly assigned U.S. patent application Ser. No. 16/282,604, filed on Feb. 22, 2019, and U.S. patent application Ser. No. 16/282,652, filed on Feb. 22, 2019, the disclosures of which are hereby incorporated by reference herein.

Figure 2A:
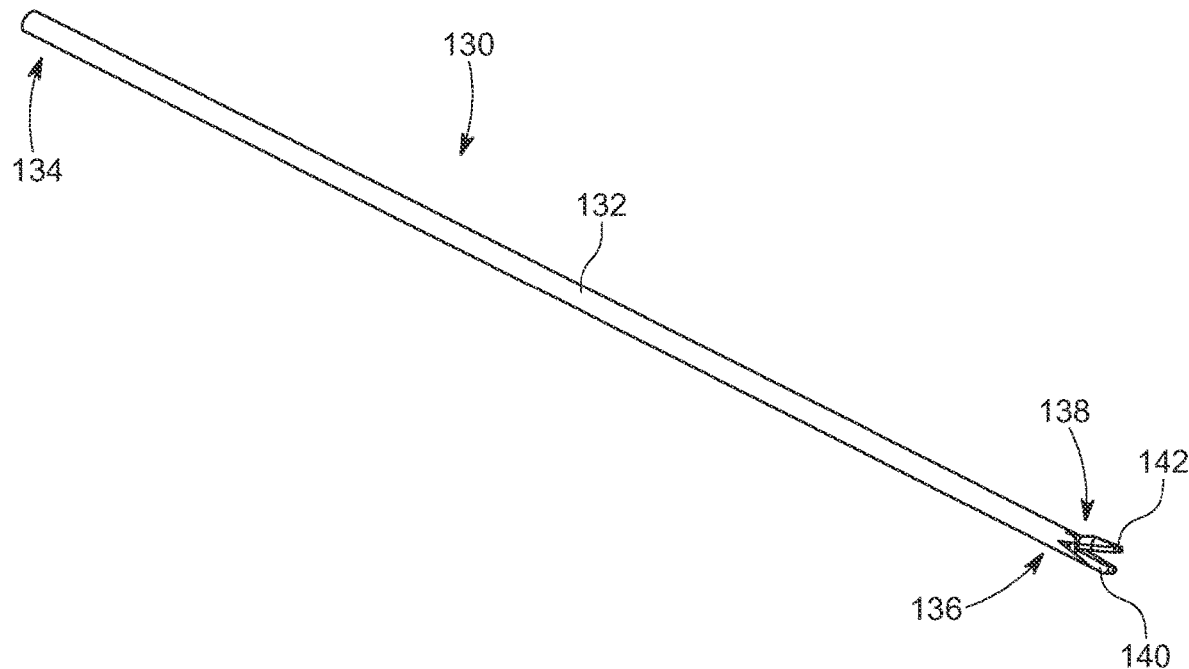
FIG. 2A is a perspective view of a distal section of a needle driver having a clamping assembly at a distal end thereof, in accordance with one embodiment of the present patent application.
Figure 2B:
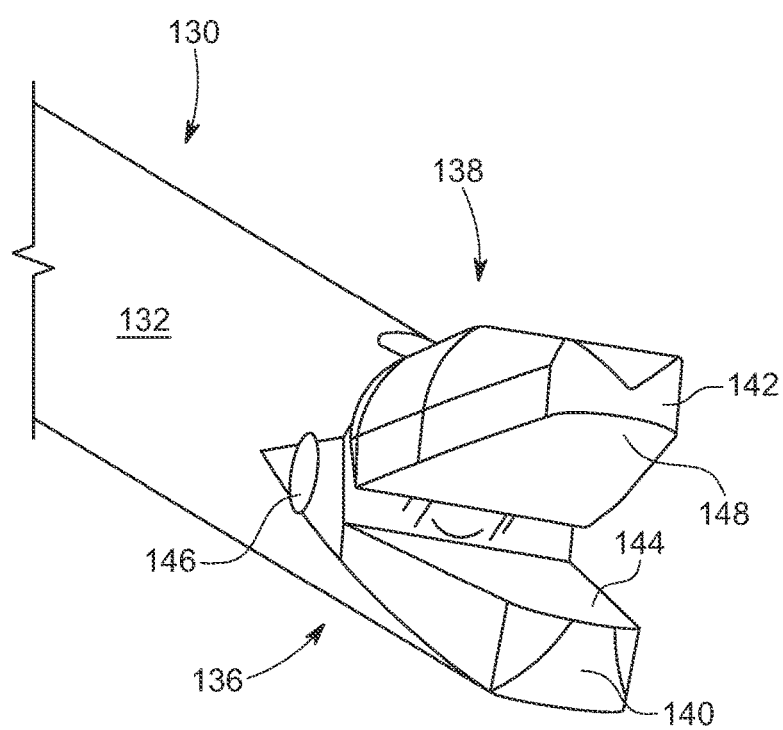
FIG. 2B is a perspective view of the clamping assembly located at a distal end of the needle driver shown in FIG. 2A.

Referring to FIGS. 2A and 2B, in one embodiment, a clamping element such as a needle driver 130 may be utilized for securing a suture needle, such as the elastic suture needle 100 shown in FIGS. 1A, 1B and 1B-1, to remove the suture needle from a suture needle package and/or to advance the suture needle through a cannula to a surgical site for performing a suturing operation. In one embodiment, the shape of the elongated body of the elastic suture needle may change as the needle driver 130 advances the suture needle through the cannula. For example, the suture needle may be an elastic suture needle that normally has a half circle shape with a first height. As the needle driver 130 advances the suture needle through a cannula having an inner diameter that is smaller than the first height of the elongated body of the suture needle (e.g., height $H_1$ shown in FIG. 1B), the inner walls of the cannula may exert an external force upon the elongated body of the suture needle whereupon the elongated body of the suture needle will flatten out or become straighter along at least one segment of the elongated body of the elastic suture needle for transforming to a smaller, second height for fitting through the smaller inner diameter of the cannula. Upon being extracted from the end of the cannula, the inner walls of the cannula no longer exert an external force upon the suture needle, whereupon the elongated body of the elastic suture needle will preferably transform back (e.g., spring back) to its original half circle shape having the first height $H_1$ (FIG. 1B).

In one embodiment, the needle driver 130 preferably includes an elongated shaft 132 having a proximal end 134 and a distal end 136 with a clamping assembly 138 that is movable between open and closed positions. In one embodiment, the clamping assembly 138 preferably includes a lower jaw 140 and an opposing upper jaw 142 that is movable between open and closed positions. In one embodiment, with the clamping assembly 138 in the open position, the lower and upper jaws 140, 142 may be guided into alignment with the tip 112 of the suture needle 100 (FIG. 1A). In one embodiment, after the lower and upper jaws are aligned with the tip of the suture needle, the jaws may be moved to the closed position for clamping and/or gripping the distal end 106 (FIG. 1A) of the suture needle with the tip 114 preferably positioned between and surrounded by the opposing lower and upper jaws.

Referring to FIG. 2B, in one embodiment, the lower jaw 140 may be stationary, rigidly secured, and/or integral to the distal end 136 of the elongated shaft 132 of the needle driver 130 so that the lower jaw 140 is fixed and does not move relative to the distal end 138 of the elongated shaft 132 of the needle driver 130. In one embodiment, the lower jaw 140 preferably includes a substantially flat top surface 144 that is adapted to be aligned with the tip 114 (FIG. 1A) of the suture needle. In one embodiment, the substantially flat top surface 144 of the lower jaw 140 may include a surface roughening such as knurling for enhancing gripping of the distal end of the elastic suture needle when the clamping assembly 138 is in the closed position.

In one embodiment, the upper jaw 142 of the clamping assembly 138 is desirably pivotally secured to the distal end 136 of the elongated shaft 132 of the needle driver 130 via a pivot 146, which pivotally secures a proximal end of the upper jaw 142 to the distal end 136 of the elongated shaft 132. The upper jaw 142 preferably includes a substantially flat bottom surface 148 that opposes the substantially flat top surface 144 of the lower jaw 140. The substantially flat bottom surface 148 of the upper jaw 142 may include surface roughening such as knurling for gripping the distal end of the elastic suture needle when the clamping assembly 138 is in the closed position.

Referring to FIGS. 1A and 2B, in one embodiment, when the lower and upper jaws 140, 142 are in the closed position for clamping, gripping and/or securing the distal end 106 of the elongated body 102 of the elastic suture needle, the top surface 144 of the lower jaw 140 engages the bottom surface 116 of the elongated body at the distal end 106 of the suture needle 100, and the bottom surface 148 of the upper jaw 142 preferably engage the top surface 114 of the elongated body 102 at the distal end 106 of the suture needle 100, with the tip 112 of the suture needle being located between the opposing jaws. In one embodiment, when the jaws are closed, the top and bottom surfaces 144, 148 of the respective lower and upper jaws 140, 142 may be spaced away from the tip 112 so that the tip is not marred, bent, damaged, or dulled by the jaws of the clamping assembly. The closed jaws preferably surround the outer perimeter of the tip as the suture needle is passed through a cannula for preventing the tip from scratching or being damaged by the inner wall of the cannula.

In one embodiment, a suture needle package may hold the elastic suture needle 100, such as the suture needle shown in FIGS. 1A and 1B, so that the tip 112 of the suture needle 100 is pre-positioned at a location that will facilitate aligning the tip 112 between the top and bottom surfaces 144, 148 of the respective lower and upper jaws 140, 142 of the clamping assembly 138 of the needle driver 130.

Figure 3A:
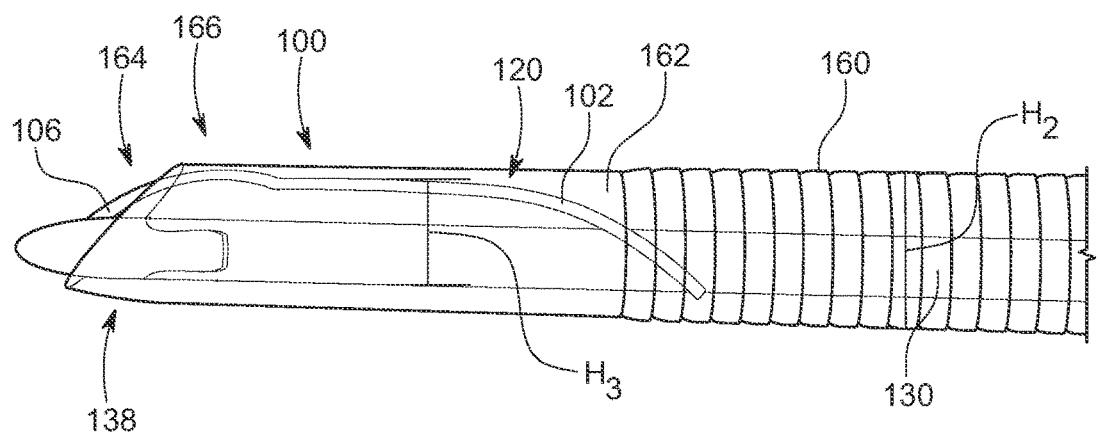
FIG. 3A shows a stage of a method of using a needle driver to advance an elastic suture needle toward a distal end of a cannula, in accordance with one embodiment of the present patent application.

Referring to FIG. 3A, in one embodiment, after the clamping assembly 138 of the needle driver 130 has been closed for clamping onto the distal end 106 of the elongated body 102 of the elastic suture needle 100, the needle driver 130 may be utilized for advancing the suture needle 100 through a cannula 160 to position the suture needle at a surgical site for performing a suturing operation. In one embodiment, the cannula 160 preferably has an elongated conduit 162 having an inner diameter that defines a second height $H_2$. The elongated conduit 162 preferably extends to an opening 164 at a distal end 166 of the cannula 160. The clamping assembly 138 of the needle driver 130, clamped onto the distal end 106 of the elongated body 102 of the suture needle 100, may be advanced toward the distal end of the conduit 162 of the cannula 160 for pulling the elastic suture needle 100 through the cannula. As the suture needle 100 is pulled by the clamping assembly 138 of the needle driver 130 toward the distal end 166 of the cannula 160, the suture needle 100 is required to fit through the smaller conduit 162 having the second height $H_2$ that is less than the original, first height $H_1$ (FIG. 1B) of the suture needle 100. Because the suture needle 100 is capable of elastically deforming, the elongated body 102 of the suture needle 100 preferably elastically deforms (e.g., straightens out, becomes flatter) as shown in FIG. 3A. In FIG. 3A, a mid-section 120 of the elongated body 102 of the elastic suture needle 100 straightens or flattens for reducing the overall height of the suture needle to a third height $H_3$ that is less than the second height $H_2$ of the conduit 162 of the cannula 160. At the smaller third height $H_3$, the transformed suture needle may pass through the smaller conduit 162 of the cannula 160. As will be described in more detail herein, the suture needle is designed to be substantially elastically deformed as it passes through the smaller cannula, changing from the first height $H_1$ to the third height $H_3$.

Figure 3B:
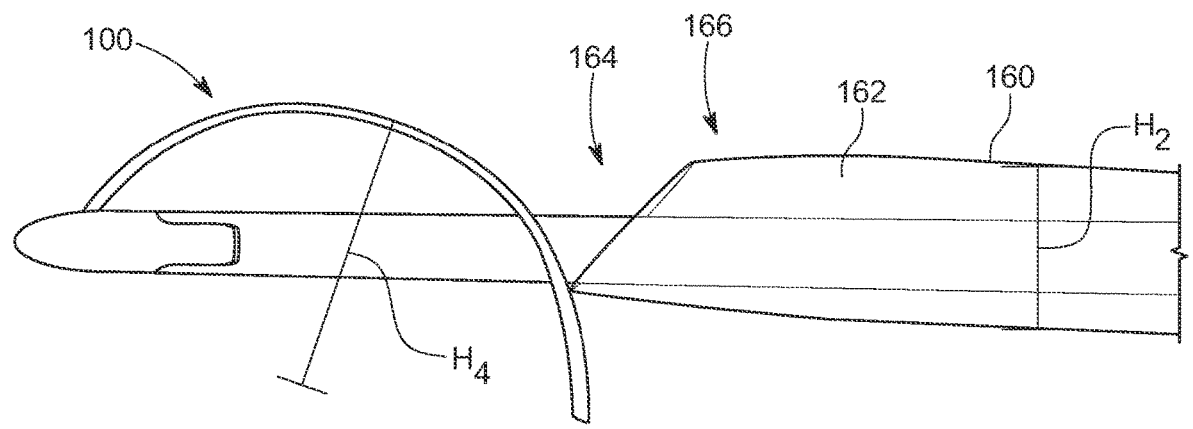
FIG. 3B shows the needle driver and the elastic suture needle of FIG. 3A after the suture needle has been advanced beyond the distal end of the cannula for being located at a surgical site, in accordance with one embodiment of the present patent application.

Referring to FIG. 3B, after the elastic suture needle 100 has been removed from the opening 164 at the distal end 166 of the cannula 160, the elastic suture needle 100 springs back to the original curved configuration (e.g., a half circle shape) having the fourth height $H_4$ that is greater than the second height $H_2$ of the conduit 162 of the cannula 160. Surgical personnel may utilize the curved suture needle 100 for performing a suturing operation at the surgical site.

In one embodiment, after being removed from the distal end 166 of the cannula 160, the elastic suture needle 100 preferably springs back to the fourth height $H_4$ that substantially matches the original, first height $H_1$ (FIG. 1B) of the suture needle. In one embodiment, the fourth height $H_4$ is about 90% of the original, first height $H_1$. In one embodiment, the fourth height $H_4$ is about 95% of the original, first height $H_1$. In one embodiment, the fourth height $H_1$ substantially matches the original, first height $H_1$.

Figure 3C:
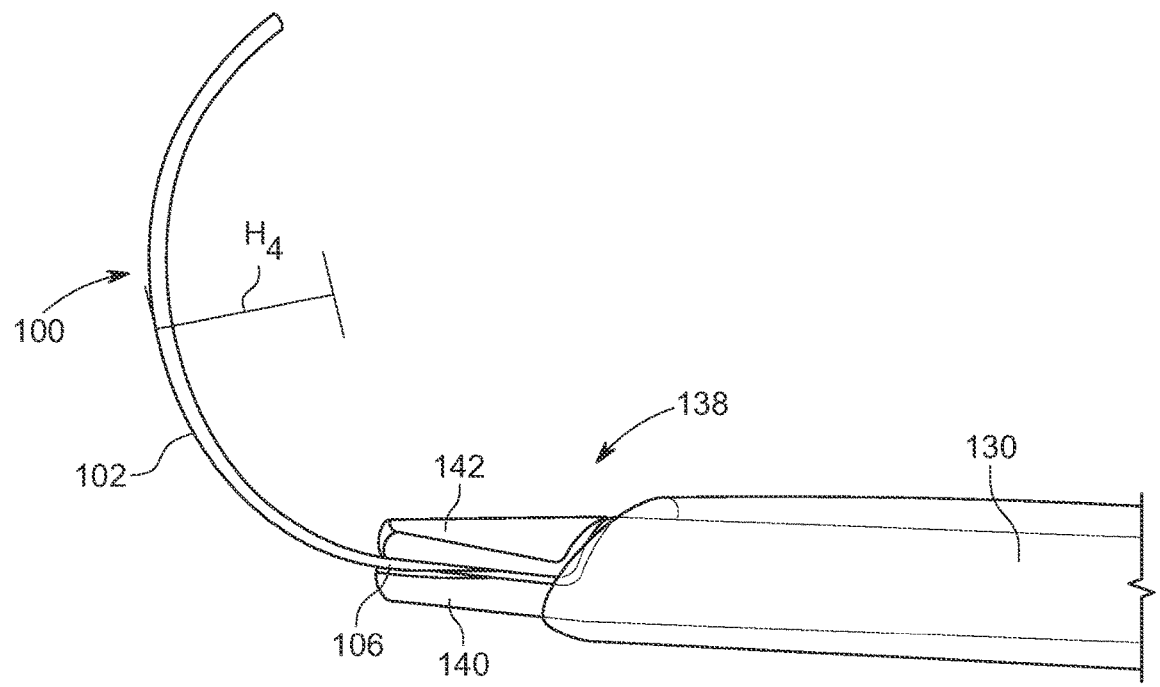
FIG. 3C shows a stage of a method of using a needle driver to retract an elastic suture needle from a surgical site and toward a proximal end of the cannula, in accordance with one embodiment of the present patent application.

Referring to FIG. 3C, in one embodiment, at the conclusion of a suturing operation, the curved suture needle 100 having the fourth height $H_4$ may be removed from a patient by retracting the suture needle through the cannula 160. In one embodiment, the clamping assembly 138 of the needle driver 130 is again closed for securing the distal end 106 of the elongated body 102 of the curved suture needle 100 between the lower jaw 140 and the upper jaw 142 of the needle driver 130.

Figure 3D:
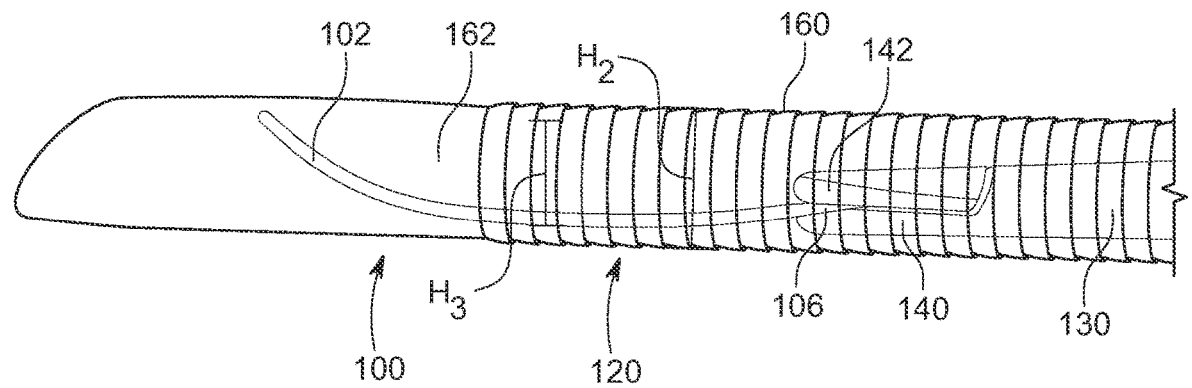
FIG. 3D shows a later stage of a method of retracting the elastic suture needle toward the proximal end of the cannula, in accordance with one embodiment of the present patent application.

Referring to FIG. 3D, in one embodiment, the needle driver 130 preferably retracts the elastic suture needle 100 through the conduit 162 of the cannula 160. Because the second height $H_2$ of the conduit of the cannula is smaller than the fourth height $H_4$ (FIG. 3B) of the suture needle 100, the mid-section 120 of the elongated body 102 of the suture needle 100 preferably straightens or flattens out to the third height $H_3$ so that the suture needle may be extracted through the conduit 162 of the cannula 160. As the elastic suture needle 100 is withdrawn through the cannula 160, the lower and upper jaws 140, 142 of the needle driver 130 preferably engage the distal end 106 of the elongated body 102 of the suture needle 100 and surround the tip 112 (FIG. 1A) of the suture needle to protect the tip from being damaged as the needle is pulled and/or retracted through the cannula 160.

In one embodiment, the suture needle is designed to exhibit elasticity for passing through a smaller cannula (e.g., a 5 mm cannula) without being plastically deformed. In one embodiment, the elastic suture needle is made of stainless steel such as high strength stainless steel. In one embodiment, knowing the yield strength and the Young's modulus for the stainless steel used to make the suture needle, the elongated body of the suture needle may be designed with flat surfaces having thickness and length dimensions that will make the suture needle elastically deformable without being plastically deformed.

The yield point for a material is the point on a stress-strain curve that indicates the limit of elastic behavior for the material and the beginning of plastic behavior. Yield strength or yield stress is the material property defined as the stress at which a material begins to deform plastically whereas yield point is the point where nonlinear (elastic+plastic) deformation begins. Prior to the yield point the material will deform elastically and will return to its original shape when the applied stress is removed. Once the yield point is passed, however, some fraction of the deformation will be permanent and non-reversible. The yield point determines the limits of performance for mechanical components, since it represents the upper limit to forces that can be applied without permanent deformation.

The Young's modulus of a material is one way to measure the modulus of elasticity of a material. A modulus of elasticity is a quantity that measures an object's resistance to being deformed elastically (i.e., non-permanently) when a stress is applied to it. The modulus of elasticity of an object is defined as the slope of its stress-strain curve in the elastic deformation region. A stiffer material will have a higher modulus of elasticity.

Specifying how stress and strain are to be measured, including directions, allows for many types of elastic moduli to be defined. Young's modulus (E) describes tensile elasticity, or the tendency of an object to deform along an axis when opposing forces are applied along that axis. It is defined as the ratio of tensile stress to tensile strain. It is often referred to simply as the elastic modulus.

In one embodiment, the elongated body of the suture needle is preferably elastically deformable from a half-circle shape to a flatter shape having a straightened section without plastically deforming the elongated body of the suture needle. As a result, when the elastic suture needle is passed through the smaller cannula and is extracted at a surgical site, the elongated body of the suture needle will preferably spring back to its original half circle shape.

Figure 4A:
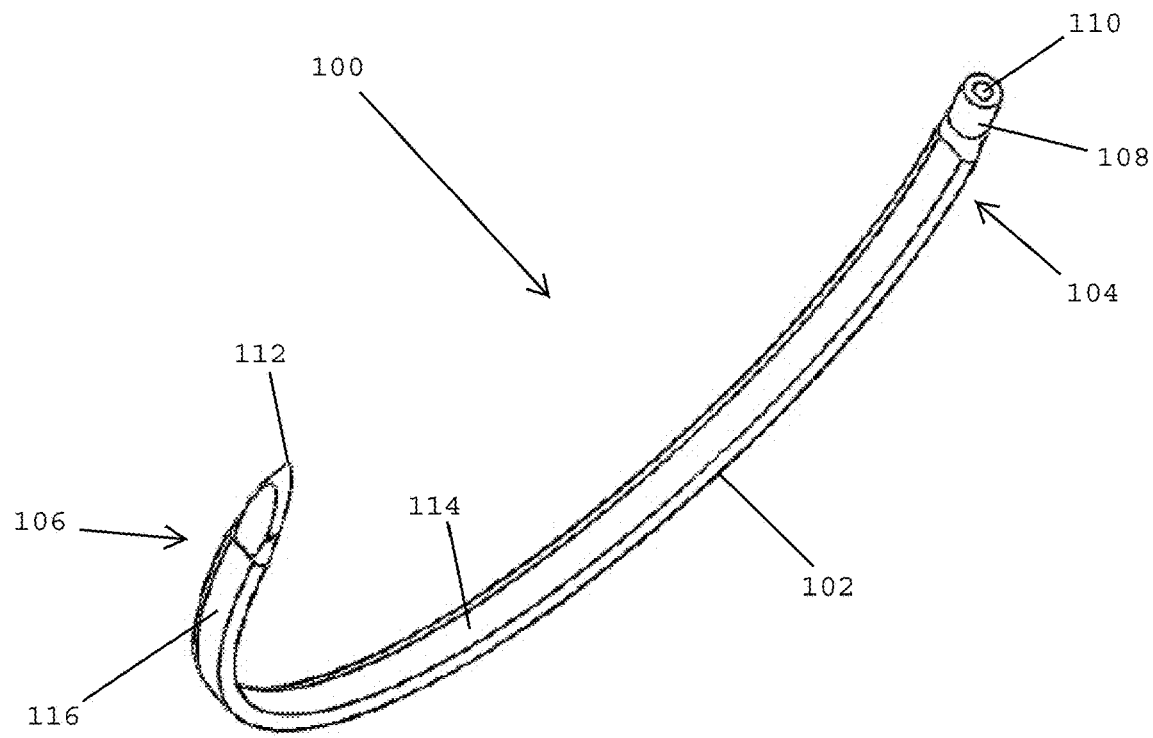
FIG. 4A is a perspective view of an elastic suture needle having an elongated body with a curved configuration, in accordance with one embodiment of the present patent application.

Referring to FIG. 4A, in one embodiment, the suture needle 100 preferably has the curved elongated body 102 that extends from the proximal end 104 to the distal end 106, a suture attachment barrel 108 having a suture attachment opening 110 located at the proximal end 104 of the elongated body 102, and the tip 112 located at the distal-most end of the suture needle. In a first configuration, the elongated body 102 of the elastic suture needle 100 is preferably curved and has the top surface 114 that extends along the concave top side of elongated body 102 and the bottom surface 116 that extends along the convexly curved bottom side of the elongated body 102.

In one embodiment, the top and bottom surfaces 114, 116 of the curved elongated body 102 preferably define the thickness T (FIG. 5) of the suture needle 100, whereby the axis for measuring the thickness T is perpendicular to the longitudinal axis of the elongated body 102 of the suture needle 100. In one embodiment, the top and bottom surfaces 114, 116 define flat surfaces that extend longitudinally and laterally over the respective top and bottom sides of the elongated body of the suture needle.

Figure 4B:
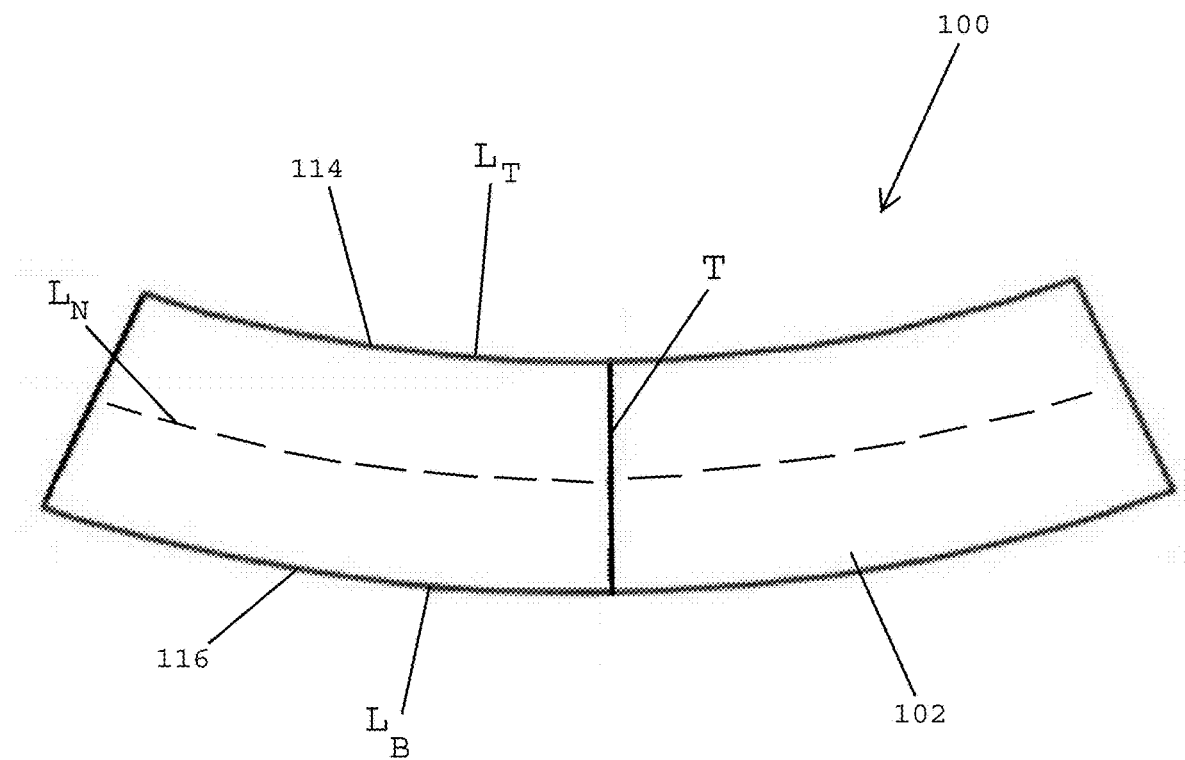
FIG. 4B is a magnified view of a mid-section of the elongated body of the elastic suture needle shown in FIG. 4A.

Referring to FIGS. 4A and 4B, in one embodiment, the elongated body 102 of the elastic suture needle 100 preferably has the neutral length $L_N$ that extends along the center of the elongated body 102 and between the proximal end 104 and the distal end 106 of the elongated body 102, the top length $L_T$ that extends along the top surface 114 of the elongated body 102, and the bottom length $L_B$ that extends along the bottom surface 116 of the elongated body 102. The axis for the neutral length $L_N$ is located between the top surface 114 and the bottom surface 116 of the elongated body 102. The distance between the flat top surface 114 and the flat bottom surface 116 preferably defines the thickness T of the elongated body 102.

Figure 5:
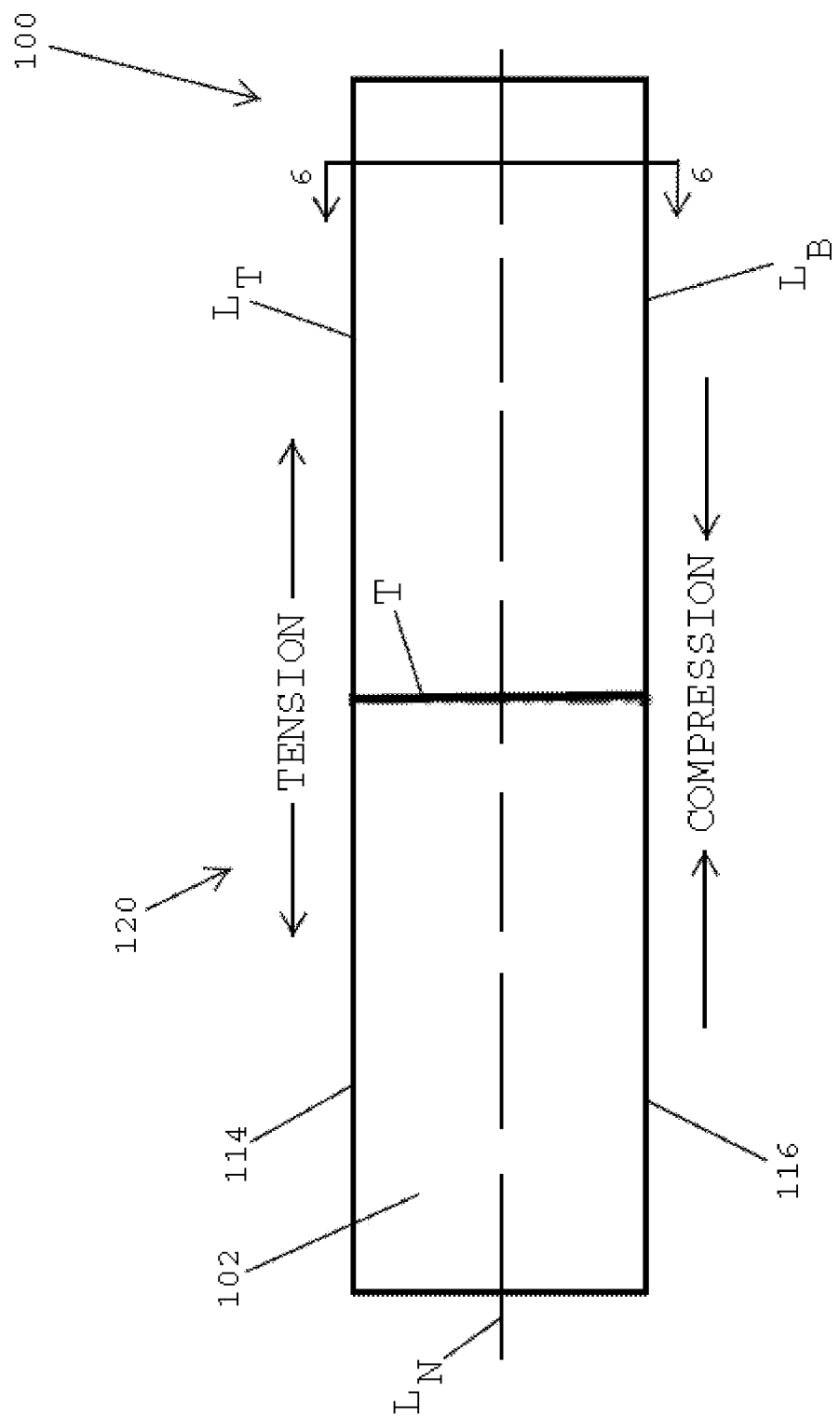
FIG. 5 is a magnified view of a mid-section of the straightened elongated body of the elastic suture needle shown in FIG. 3A.

Referring to FIG. 5, in one embodiment, the suture needle 100, made of materials having a known yield strength and a known Young's modulus, is designed to be elastic so that it can be transformed from the half circle configuration of FIGS. 4A and 4B to the flattened or straightened configuration (mid-section 120) of FIG. 3A without substantially plastically deforming the elongated body 102 of the suture needle. As a result, when external forces are no longer applied to the elongated body 102 of the suture needle, the elongated body will substantially spring back from the straightened configuration of FIGS. 3A and 5 to the original half circle shape shown in FIGS. 4A-4B.

Referring to FIG. 5, in one embodiment, when the mid-section 120 (FIG. 3A) of the elongated body 102 of the suture needle 100 is straightened for passing through a smaller cannula, tension and compression forces are applied at the respective top and bottom surfaces 114, 116 of the elongated body 102 of the suture needle 100. For the straightened mid-section 120 of the elongated body 102 shown in FIG. 5, the top surface 114 of the elongated body 102 is under tension. The bottom surface 116 of the elongated body 102 is under compression. The part of the elongated body 102 that extends along the axis that defines the neutral length $L_N$ is under neither tension nor compression. The elastic strain calculation associated with transforming the half circle suture needle (FIGS. 4A-4B) to the straightened suture needle (FIGS. 3A and 5) may be calculated using the equation $\varepsilon=\Delta L/L_N$, where $\Delta L$ is the change in the top length $L_T$ of the suture needle at the top surface 114 of the elongated body or the change in the bottom length $L_B$ of the suture needle at the bottom surface 116 of the elongated body, and $L_N$ is the neutral length of the elongated body of the suture needle that is mid-way between the top and bottom surfaces 114, 116 of the elongated body.

For a half circle suture needle, the diameter d of a circle may be calculated using the following equation $d=2*L_N/\pi$, where $L_N$ is the neutral length of the elongated body of the suture needle.

The strain associated with straightening out the curved needle is calculated using the following equation: $\varepsilon=[\frac{1}{2}\pi(d+\frac{1}{2}T)-\frac{1}{2}\pi d]/(\frac{1}{2}\pi d)$, where $\frac{1}{2}\pi(d+\frac{1}{2}T)$ is the length at the outside of the suture needle, $\frac{1}{2}\pi d$ is the length $L_N$ of the neutral axis of the elongated body of the suture needle, and T is the thickness of the elongated body of the suture needle that extends from the flat top surface 114 to the flat bottom surface 116 (FIG. 5) of the elongated body.

In one embodiment, a suture needle made of high strength stainless steel may be designed to exhibit elasticity and prevent plastic deformation and loss of the original curvature. In one embodiment, the minimum elastic strain that a suture needle is required to exhibit to prevent plastic deformation and loss of its original curvature is calculated using the following equation $\varepsilon=\pi T/4L_N$, where T is the thickness of the elongated body of the suture needle measured between the top and bottom flat surfaces of the elongated body, and $L_N$ is the neutral length of the elongated body of the suture needle.

Controlling for engineering properties such as yield strength and Young's modulus, the maximum amount of stress that may be exerted upon a suture needle while maintaining elasticity and preventing plastic deformation may be calculated using the following equation $\sigma=(\pi T/4L_N)*E$, where $\sigma$ is the Yield Strength of the material, and E is the Young's Modulus of the material.

Rearranging the above equation, a ratio for the maximum thickness T of the elongated body to the neutral length $L_N$ of the elongated body may be calculated using the following equation $T/L_N<(4*\sigma)/(\pi E)$, where T is the thickness of the elongated body of the suture needle, $L_N$ is the neutral length of the elongated body of the suture needle, $\sigma$ is the Yield Strength of the material used to make the suture needle, and E is the Young's modulus of the material used to make the suture needle.

Figure 6:
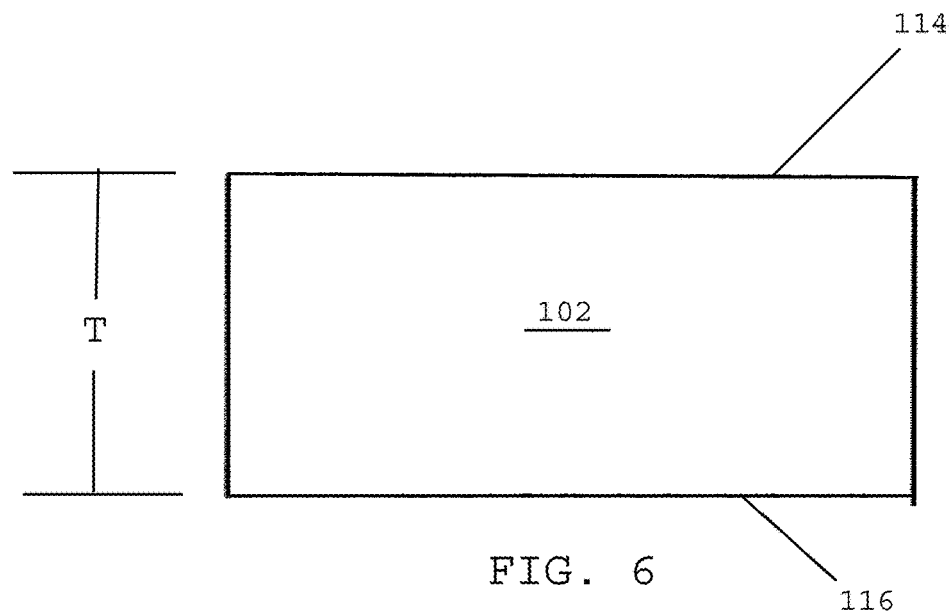
FIG. 6 is a cross-sectional view of the elongated body of the suture needle shown in FIG. 5, the elongated body having a flat top surface and a flat bottom surface.

Referring to FIG. 6, in one embodiment, the elongated body 102 of an elastic suture needle has a substantially flat top surface 114 and a substantially flat bottom surface 116. The substantially flat top and bottom surfaces 114, 116 define the thickness T of the elongated body 102.

Figure 7:
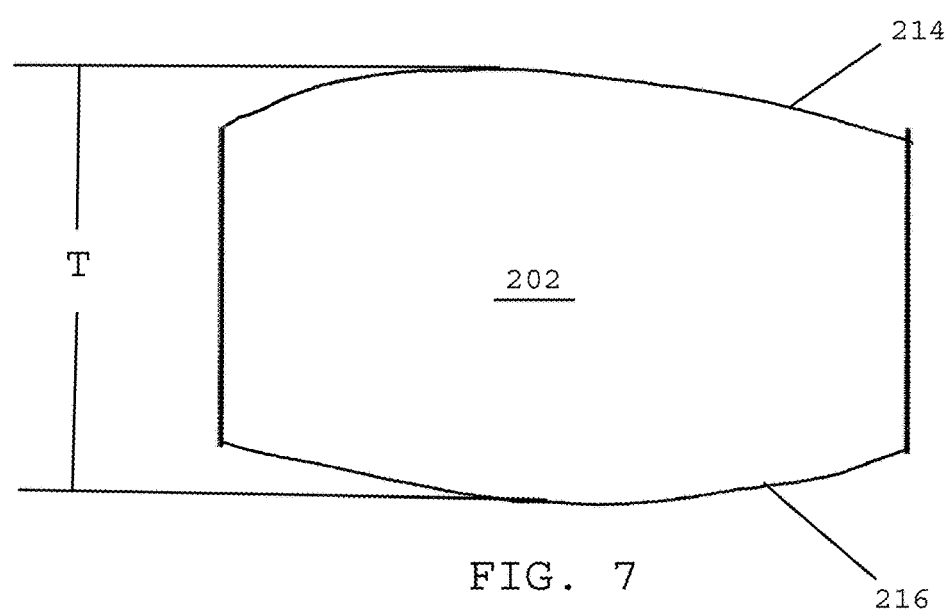
FIG. 7 is a cross-sectional view of an elongated body of a suture needle, the elongated body having a convex top surface and a convex bottom surface, in accordance with one embodiment of the present patent application.

Referring to FIG. 7, in one embodiment, an elongated body 202 of an elastic suture needle has a convex top surface 214 and a convex bottom surface 216. The thickness T of the elongated body 202 is defined by the distance between the highest part of the convex top surface 214 and the lowest part of the convex bottom surface 216.

Figure 8:
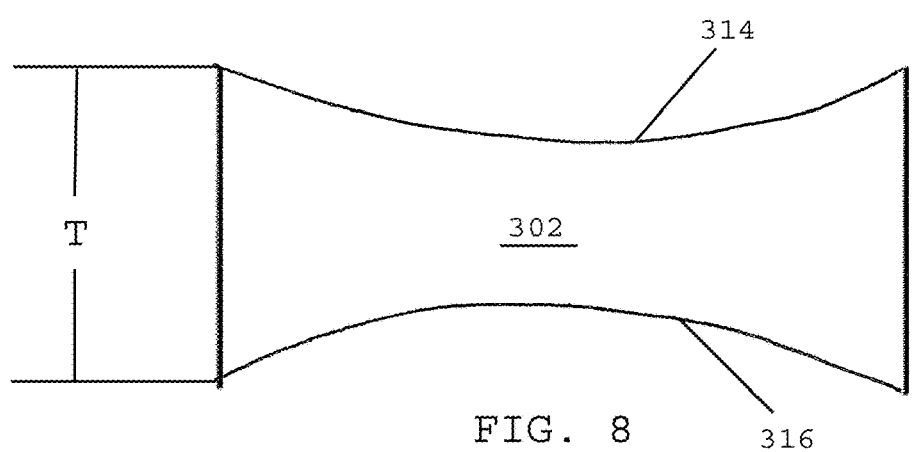
FIG. 8 is a cross-sectional view of an elongated body of a suture needle, the elongated body having a concave top surface and a concave bottom surface, in accordance with one embodiment of the present patent application.

Referring to FIG. 8, in one embodiment, an elongated body 302 of an elastic suture needle has a concave top surface 314 and a concave bottom surface 316. The thickness T of the elongated body 302 is defined by the distance between the highest part of the concave top surface 214 and the lowest part of the concave bottom surface 216.

Figure 9:
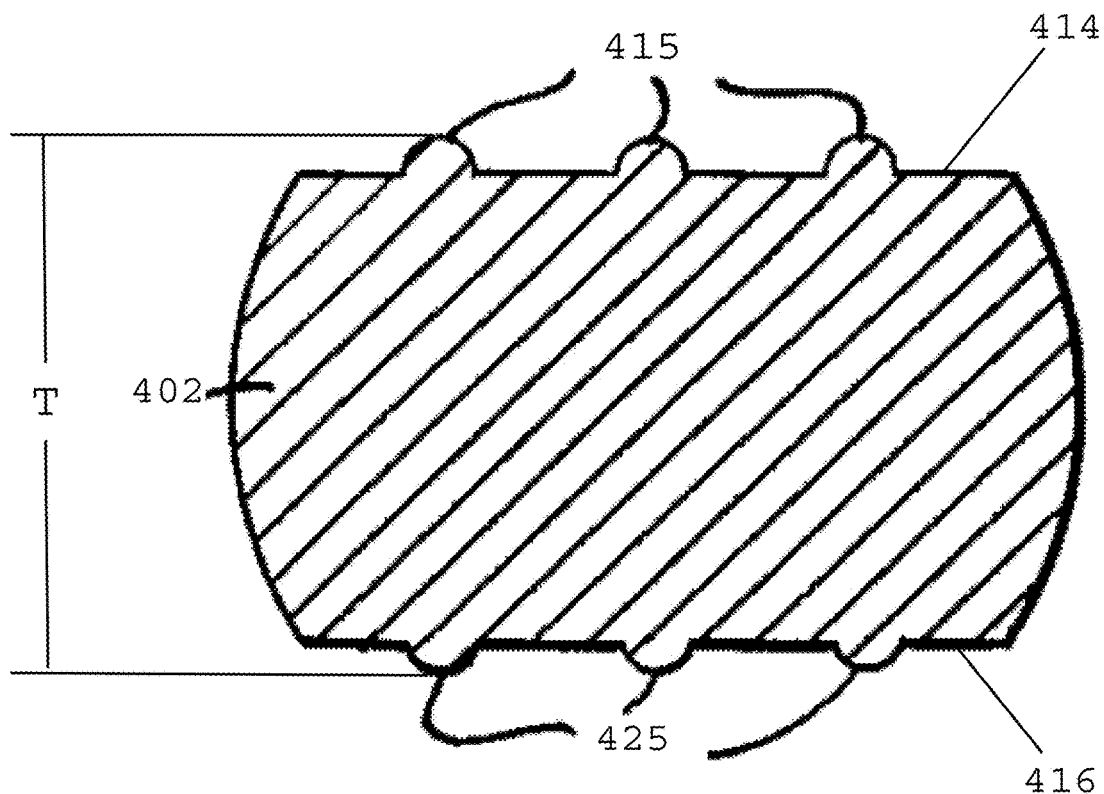
FIG. 9 is a cross-sectional view of an elongated body of a suture needle, the elongated body having a top surface with top ribs and a bottom surface with bottom ribs, in accordance with one embodiment of the present patent application.

Referring to FIG. 9, in one embodiment, an elongated body 402 of an elastic suture needle has a top surface 414 with top ribs 415 and a bottom surface 416 with bottom ribs 425, as disclosed in commonly assigned U.S. Pat. No. 3,160,157 to Chisman, the disclosure of which is hereby incorporated by reference herein. The thickness T of the elongated body 402 is defined by the distance between the outermost part of the top ribs 415 and the outermost part of the bottom ribs 425.

Figure 10:
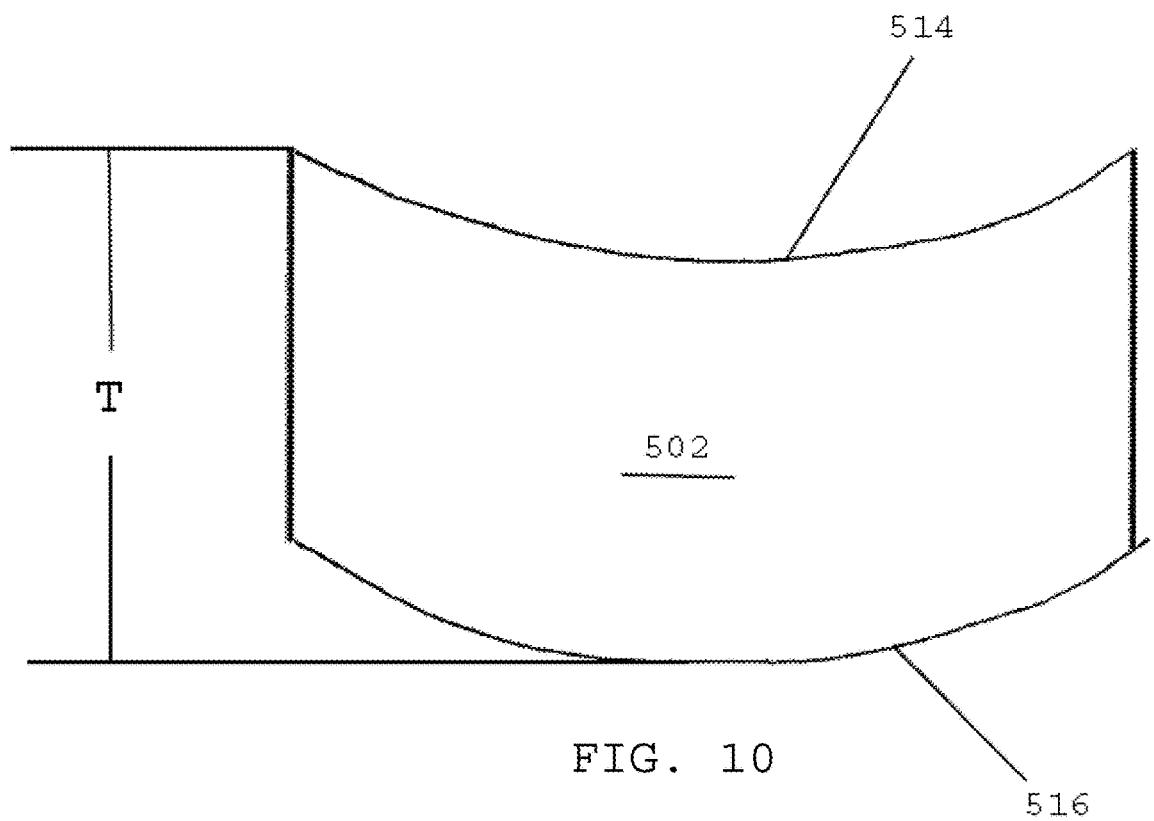
FIG. 10 is a cross-sectional view of an elongated body of a suture needle, the elongated body having a concave top surface and a convex bottom surface, in accordance with one embodiment of the present patent application.

Referring to FIG. 10, in one embodiment, an elongated body 502 of an elastic suture needle has a concave top surface 514 and a convex bottom surface 516. The thickness T of the elongated body 502 is defined by the distance between the highest part of the concave top surface 514 and the lowest part of the convex bottom surface 516.

Figure 11:
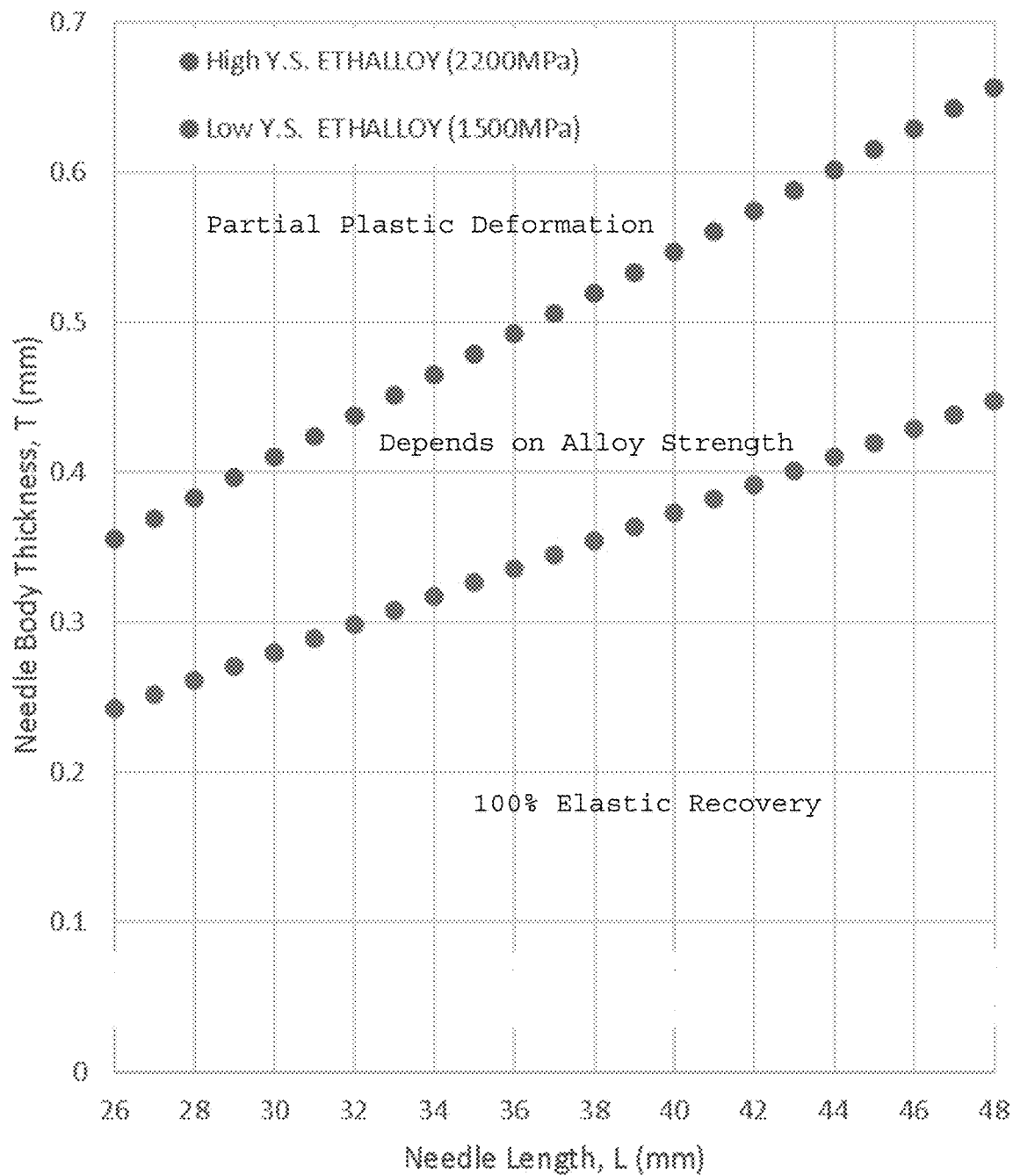
FIG. 11 is a graph plotting the needle body thickness and needle body length dimensions to achieve elastic recovery for suture needles, in accordance with one embodiment of the present patent application.

FIG. 11 is a graph that plots the thickness and length dimensions that may be used for making suture needles that will elastically deform but not plastically deform during passage through smaller cannulas used in minimally invasive surgery. Knowing the yield strength and the Young's modulus of stainless steels used to make the suture needles, the elongated body's thickness T versus the elongated body's neutral length $L_N$ may be designed into suture needles to achieve elastic recovery during minimally invasive surgery. For example, a suture needle made of high yield strength ETHALLOY Needle Alloy (2200 MPa) having an elongated body thickness T of <0.25 mm and an elongated body neutral length $L_N$ of 30 mm will achieve complete elastic recovery after passing through a smaller cannula, however, a suture needle made of the same high yield strength ETHALLOY Needle Alloy (2200 MPa) having an elongated body thickness T of 0.51 mm inches and an elongated body neutral length $L_N$ of 30 mm will suffer some partial plastic deformation when passing through the smaller cannula.

The stainless steels used to make the elastic suture needles disclosed herein may include martensitic stainless steels (420SS), austenitic stainless steels (302SS), and martensitic-aged (mar-aged) stainless steels (455SS).

Martensitic stainless steels (420SS) can be high-carbon or low-carbon steels built around the Type 420 composition of iron, 12% chromium, and up to 0.4% carbon. Martensitic stainless steel is hardenable by heat treatment (e.g., by quenching, or by quenching and tempering). The alloy composition and the high cooling rate of quenching enable the formation of martensite. Tempered martensite provides steel with good hardness and high toughness. It is often used for making medical devices and tools such as scalpels, razors and suture needles. See the definition of Martensitic stainless steel at en.wikipedia.org.

Austenitic stainless steels (302SS) possess austenite as their primary crystalline structure. The austenite crystalline structure is achieved by sufficient additions of the austenite stabilizing elements nickel, manganese and nitrogen. Due to their crystalline structure austenitic steels are not hardenable by heat treatment and are essentially non-magnetic. See the definition of Austenitic stainless steel at en.wikipedia.org. Nevertheless, exceptionally high strength may be achieved via work hardening especially in the wire drawing process used to produce feedstock for needle manufacturing.

Martensitic-aged (mar-aged) stainless steels (455SS) are steels that are known for possessing superior strength and toughness without losing malleability. The "aging" portion of the word Mar-aged refers to the extended heat-treatment process. These steels are a special class of low-carbon, ultra-high-strength steels that derive their strength not from carbon, but from precipitation of intermetallic compounds. Typically, the principal alloying element is 7 to 25 wt. % nickel. Secondary alloying elements, which include cobalt, molybdenum and titanium, are added to produce intermetallic precipitates. See the definition of Maraging steel at en.wikipedia.org.

One type of martensitic-aged alloy that was specifically developed for suture needles and that provides levels of strength far exceeding that of alloys previously used for making suture needles is sold under the registered trademark ETHALLOY Needle alloy. The ETHALLOY Needle Alloy is strengthened by a combination of work hardening and thermal processing (precipitation strengthening).

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. An elastic suture needle comprising an elongated body having a proximal end, a distal end, a length extending from the proximal end to the distal end, a top surface extending along the length of said elongated body, and a bottom surface extending along the length of said elongated body, wherein said elongated body has a width that remains constant between said top and bottom surfaces of said elongated body, and wherein said elongated body has dimensions that are calculated using the equation $T/L_N < (4*\sigma)/(\pi E)$, where T is the thickness of said elongated body, $L_N$ is the length of the neutral axis of said elongated body, σ is the yield strength of said elongated body, and E is the Young's modulus of said elongated body;

said elastic suture needle further comprising a tip that extends distally beyond the distal end of said elongated body, wherein said elongated body is curved and said tip is straight;

a suture attachment barrel that extends proximally beyond the proximal end of said elongated body, wherein said suture attachment barrel has a thickness that is greater than the thickness T of said elongated body.

2. The elastic suture needle as claimed in claim 1, wherein said elongated body comprises stainless steel.

3. The elastic suture needle as claimed in claim 2, wherein said stainless steel is selected from the group of stainless steels consisting of martensitic stainless steels, austenitic stainless steels, and martensitic-aged (mar-aged) stainless steels.

4. The elastic suture needle as claimed in claim 1, wherein said top surface of said elongated body includes a flat top surface that extends along the length of said elongated body, and wherein said bottom surface of said elongated body include a flat bottom surface that extends along the length of said elongated body.

5. The elastic suture needle as claimed in claim 4, wherein the thickness T of said elongated body is a distance between said flat top surface of said elongated body and said flat bottom surface of said elongated body.

6. The elastic suture needle as claimed in claim 1, wherein said elongated body is curved with said top surface of said elongated body defining a concave aspect of said curved elongated body and said bottom surface defining a convex aspect of said curved elongated body.

7. The elastic suture needle as claimed in claim 1, wherein said elongated body comprises martensitic-aged stainless steel having a yield strength of about 1500-2200 MPa and a Young's modulus of about 200-205 GPa.

8. The elastic suture needle as claimed in claim 1, wherein said tip that extends distally beyond the distal end of said elongated body has a first length and said suture attachment barrel that extends proximally beyond the proximal end of said elongated body has a second length, and wherein the first length of said tip is greater than the second length of said suture attachment barrel.

9. The elastic suture needle as claimed in claim 1, wherein said elongated body has a center located along the neutral axis of said elongated body that is equidistant from the proximal and distal ends of said elongated body, wherein a free end of said tip is located a first distance from the center of said elongated body and a free end of said suture attachment barrel is located a second distance from the center of said elongated body, and wherein the first distance defined by the free end of said tip is greater than the second distance defined by the free end of said suture attachment barrel.

10. The elastic suture needle as claimed in claim 1, wherein said tip is integrally formed with the distal end of said elongated body and said suture attachment barrel is integrally formed with the proximal end of said elongated body.

11. An elastic suture needle comprising an elongated stainless steel body having a proximal end, a distal end, a length extending from the proximal end to the distal end, a flat top surface extending along the length of said elongated stainless steel body, and a flat bottom surface extending along the length of said elongated stainless steel body, wherein said elongated stainless steel body has a width that remains constant between said top and bottom surfaces of said elongated stainless steel body, and wherein said elongated stainless steel body has dimensions that are calculated using the equation $T/L_N < (4*\sigma)/(\pi E)$, where T is the thickness defined as a distance from said flat top surface to said flat bottom surface of said elongated stainless steel body, $L_N$ is the length of the neutral axis of said elongated stainless steel body, $\sigma$ is the yield strength of said elongated stainless steel body, and E is the Young's modulus of said elongated stainless steel body;
said elastic suture needle further comprising a suture attachment barrel that extends proximally beyond the proximal end of said elongated stainless steel body, wherein said suture attachment barrel has a thickness that is greater than the thickness T of said elongated stainless steel body.

12. The elastic suture needle as claimed in claim 11, wherein said elongated stainless steel body is curved with said flat top surface of said elongated stainless steel body defining a concave aspect of said curved elongated body and said flat bottom surface of said elongated stainless steel body defining a convex aspect of said curved elongated body.

13. The elastic suture needle as claimed in claim 11, wherein said stainless steel is selected from the group of stainless steels consisting of martensitic stainless steels, austenitic stainless steels, and martensitic-aged (mar-aged) stainless steels.

14. The elastic suture needle as claimed in claim 11, wherein said elongated stainless steel body comprises martensitic-aged stainless steel having a yield strength of about 1500-2200 MPa and a Young's modulus of about 200-205 GPa.

15. The elastic suture needle as claimed in claim 11, wherein said elastic suture needle comprises:
a tip that extends distally beyond the distal end of said elongated stainless steel body, wherein said elongated stainless steel body is curved and said tip is straight;
said suture attachment barrel being located at a proximal-most end of said elastic suture needle.

16. The elastic suture needle as claimed in claim 15, wherein said tip that extends distally beyond the distal end of said elongated stainless steel body has a first length and said suture attachment barrel that extends proximally beyond the proximal end of said elongated stainless steel body has a second length, and wherein the first length of said tip is greater than the second length of said suture attachment barrel.

17. The elastic suture needle as claimed in claim 15, wherein said elongated stainless steel body has a center located along the neutral axis of said elongated stainless steel body that is equidistant from the proximal and distal ends of said elongated body, wherein a free end of said tip is located a first distance from the center of said elongated body and a free end of said suture attachment barrel is located a second distance from the center of said elongated body, and wherein the first distance defined by the free end of said tip is greater than the second distance defined by the free end of said suture attachment barrel.

18. The elastic suture needle as claimed in claim 15, wherein said tip is integrally formed with the distal end of said elongated stainless steel body and said suture attachment barrel is integrally formed with the proximal end of said elongated stainless steel body.

\* \* \* \* \*